United States Patent [19]

Itaya et al.

[11] Patent Number: 4,853,776
[45] Date of Patent: Aug. 1, 1989

[54] FABRIC INSPECTING METHOD AND APPARTUS FOR DETECTING FLAWS

[75] Inventors: Hisao Itaya; Toshihiko Okada; Morishige Hata; Shunji Koike; Takahiro Onishi, all of Kyoto, Japan

[73] Assignee: Gunze Ltd., Kyoto, Japan

[21] Appl. No.: 176,540

[22] Filed: Apr. 1, 1988

[30] Foreign Application Priority Data

Apr. 3, 1987 [JP] Japan .................................. 62-083383

[51] Int. Cl.$^4$ ............................................. H04N 7/18
[52] U.S. Cl. ........................................ 358/106; 26/70; 358/101
[58] Field of Search .................... 358/101, 106; 26/70; 356/429, 430, 231

[56] References Cited

U.S. PATENT DOCUMENTS

| | | | |
|---|---|---|---|
| 2,935,559 | 5/1960 | Dornier | 358/106 |
| 2,984,699 | 5/1961 | Dornier | 358/106 |
| 3,419,677 | 12/1968 | Fiori | 358/106 |
| 3,715,476 | 2/1973 | Watanabe | 358/106 |
| 4,583,181 | 4/1986 | Gerber | 358/106 |
| 4,748,334 | 5/1988 | Kobayashi | 356/431 |

Primary Examiner—Howard W. Britton
Attorney, Agent, or Firm—Armstrong, Nikaido, Marmelstein Kubovcik & Murray

[57] ABSTRACT

An inspection method and apparatus for searching a fabric in strip form to find lump type and void type flaws on both faces of the fabric. Strobes and image pickup elements are arranged at opposite sides of the fabric in transportation. The strobes at one side of the fabric are caused to emit light, and the image pickup elements at the same side detect light reflected by the fabric while the image pickup elements at the other side detect light passing through the fabric.

6 Claims, 12 Drawing Sheets

FABRIC INSPECTING METHOD AND APPARTUS FOR DETECTING FLAWS

BACKGROUND OF THE INVENTION (1) Field of the Invention

The present invention relates to a fabric inspecting method and apparatus for detecting lump type flaws such as soiled spots, strands, knots and swells, and void type flaws such as circular holes, runs and cuts formed on textile and other fabrics.

(2) Description of the Prior Art

Flaws present on textile and other fabrics to be inspected include various types such as the lump type and void type, which makes it difficult to automate the flaw detecting operation. In earlier times, the flaw detection was carried out visually, through the eyes of the worker, while transporting fabrics. The inspection by the human eye did not provide for high efficiency, and was an obstacle to mass production.

A fabric inspecting apparatus for automatically detecting flaws on fabrics is described in "Kako Gijutsu" (or Processing Technology) published in 1983, Vol. 18, No. 11, pages 32 and 33. According to this apparatus, a laser beam emitted from a laser source is turned by a rotating mirror to scan a fabric transversely, and light reflection and transmission from the fabric are detected by two line sensors. Flaws are detected by processing detection signals from the line sensors.

This fabric inspecting system requires the rotating mirror for turning the laser beam to scanning directions, and a drive source for rotating the mirror. This results in a complicated construction, and yet the system is unable to detect lump type flaws present on the back face of the fabric.

SUMMARY OF THE INVENTION

A primary object of the present invention, therefore, is to provide an improved fabric inspecting method capable of detecting flaws on both faces of a fabric and other material under inspection.

Another object of the invention is to provide a fabric inspecting apparatus capable of detecting flaws on both faces of a material under inspection without any rotating components included in a detecting section of the apparatus.

The first-mentioned object of the invention is fulfilled by a method comprising the steps of transporting the fabric through a space between a plurality of strobes and image pickup elements, and alternately causing the strobes at one side of the fabric and the strobes at the other side to emit light, causing the image pickup elements at both sides of the fabric to read strobe light passing through the fabric and strobe light reflected by the fabric at times of light emission from the strobes, detecting a flaw on the fabric by electrically processing images provided by the image pickup elements, and marking the fabric at a position of the flaw.

The step of detecting a flaw may include the step of detecting the flaw again by stopping the fabric, transporting the fabric a predetermined distance backward and then advancing the fabric at low speed.

The second object of the invention is fulfilled by an apparatus comprising transport means for transporting the fabric longitudinally thereof, a dark room through which the fabric is transported, a plurality of strobe means arranged in the dark room to emit light to the fabric in transportation alternately from opposite sides thereof, image pickup means associated with the strobe means to pick up strobe light passing through the fabric and reflected by the fabric, processing means for electrically processing images provided by the image pickup means, and marking means for marking a flaw position of the fabric in response to a flaw signal received from the processing means.

In a preferred embodiment of the invention, the strobe means are arranged at both sides of the fabric and outside fields of view of the image pickup means. The image pickup means are provided in a plural number and arranged at intervals transversely of the fabric.

The marking means may be controlled to apply marks to the flaw position and to a selvage of the fabric.

According to the method and apparatus of the present invention, the strobes and image pickup elements, respectively, are arranged at opposite sides of the fabric under inspection. The strobes are actuated to emit light in turns, and the image pickup elements at both sides pick up the reflected light and transmission light simultaneously. Consequently, both the lump type and void type flaws developed in complex forms on the fabric are detected in a reliable manner. The strobes and image pickup elements are fixed in position, and this feature eliminates the possibility of reducing the detecting precision.

Further, since the strobes emit light from both sides of the fabric, all flaws on both faces of the material under inspection are detected without fail, which contributes to improved product qualities.

Where there is no flaw, the material under inspection is transported at high speed, thereby allowing the inspection to be carried out with high efficiency without relying on a manual operation.

BRIEF DESCRIPTION OF THE DRAWINGS

These and other objects, advantages and features of the invention will become apparent from the following description thereof taken in conjunction with the accompanying drawings which illustrate a specific embodiment of the invention. In the drawings.

DESCRIPTION OF THE PREFERRED EMBODIMENT

Figure 1:
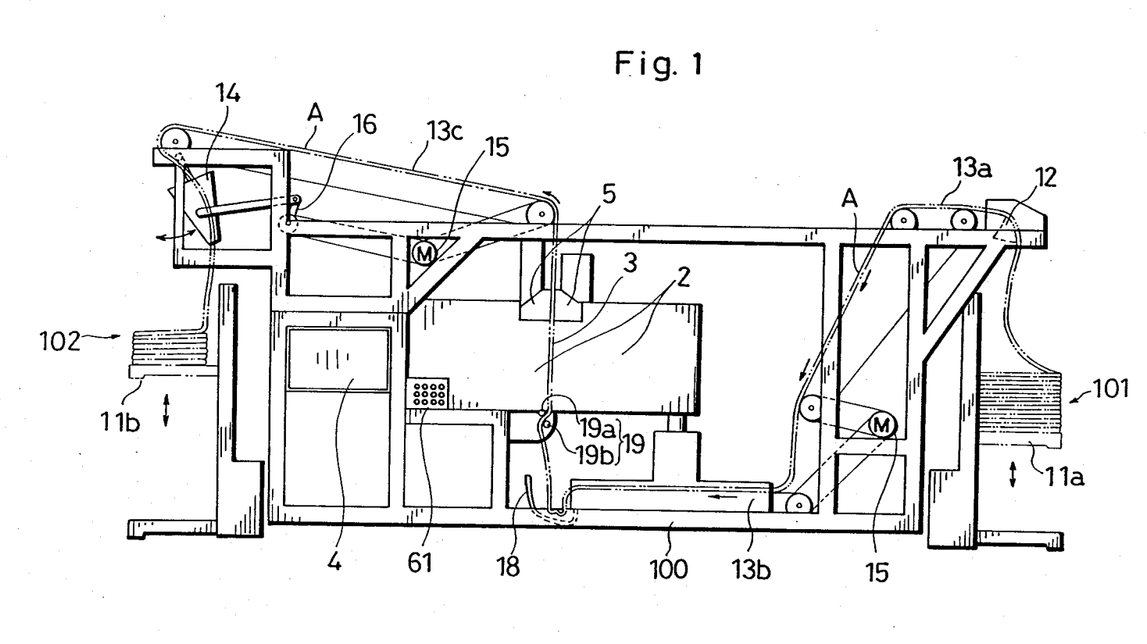
FIG. 1 is a schematic view of a fabric inspecting apparatus according to one embodiment of the invention.

FIG. 1 schematically shows an overall construction of a fabric inspecting apparatus embodying the present invention. This apparatus a main frame 100, a supply section 101 provided at the righthand side of the main frame 100 for supplying a fabric A for inspection, and a receiving section 102 at the lefthand side of the main frame 100 for receiving the fabric A after the inspection. The fabric A is transported from the supply section 101 to the receiving section 102 by a transport system 1. The inspecting apparatus further comprises a dark room 2 including a slit 3 extending along the transport system 1 for allowing passage of the fabric A, a processing device 4 for analyzing images of the fabric A picked up by TV cameras to determine presence and absence of flaws, and marker devices 5 for applying marks to flaw positions in response to signals output from the processing device 4.

The fabric supply section 101 and fabric receiving section 102 include fabric tables 11a and 11b urged upward by springs mounted inside, respectively. The tables 11a and 11b are vertically movable by the elastic force of the springs according to the weight of the fabric A. In other words, the tables 11a and 11b move upward as the amount of fabric A mounted thereon decreases, and downward as the amount thereof increases. Consequently, the fabric as folded on either table 11a or 11b has a top face thereof constantly at the same height. The mechanism for vertically moving the table 11a or 11b may comprise a sensor for detecting the amount of fabric A and a drive unit for forcibly moving the table 11a or 11b up and down. Above the table 11a of the supply section 101 is a triangular takeup roller 12, and three belt conveyors 13a-13c are arranged from the roller 12 to the table 11b of the receiving section 102. The intermediate belt conveyor 13b is disposed in a lower position centrally of the apparatus. The third belt conveyor 13c has a forward end located substantially directly over a rear end of the intermediate belt conveyor 13b. The rear end of the third belt conveyor 13c is located above the table 11b of the receiving section 102, and is continuous with a swing folding device 14. This device 14 has a lower portion thereof oscillatable within a width of the table 11b by a link 16 connected to a drive motor 15, whereby the fabric A rests folded on the table 11b.

The dark room 2 is disposed between the belt conveyors 13b and 13c, and the fabric A advances through the slit 3 extending through a central position of the dark room 2. In this embodiment, the dark room 2 is box-shaped and is dividable at the slit 3 into two, right and left halves in FIG. 1. The dark room 2 is opened for passage of fabric A by moving the right half of the dark room 2.

Figure 2A:
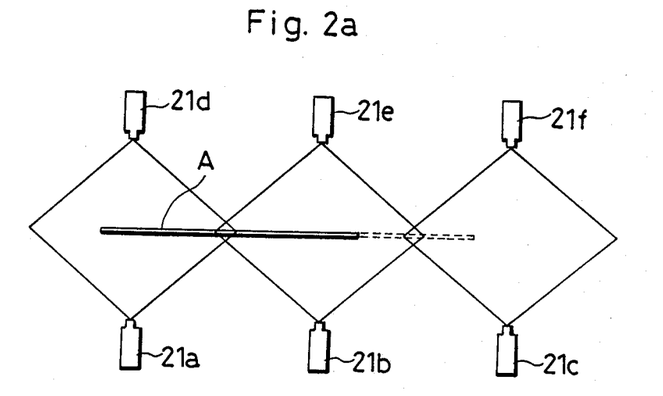
FIG. 2(a) is a plan view showing an arrangement of TV cameras constituting part of the fabric inspecting apparatus.
Figure 3:
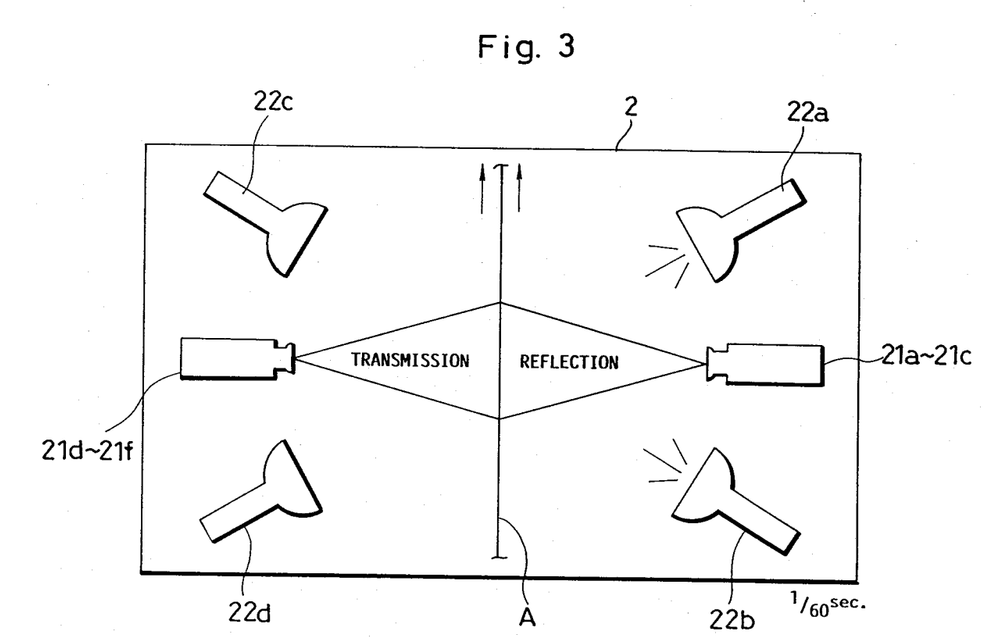
FIG. 3 is a side view of a dark room showing a state in which strobes at one side emit light to the fabric.

As shown in FIGS. 2 and 3 houses a total of six TV cameras 21a-21f, three opposed to each face of the fabric A and arranged at intervals transversely of the fabric A. The TV cameras 21a-21f each include a CCD acting as image pickup element for obtaining images of both faces of the fabric A. Four groups of strobes 22a-22b, a total of 16 strobes, are disposed above and below the middle TV cameras 21b and 21e for illuminating all fields of view of TV cameras 21a21f.

Figure 5:
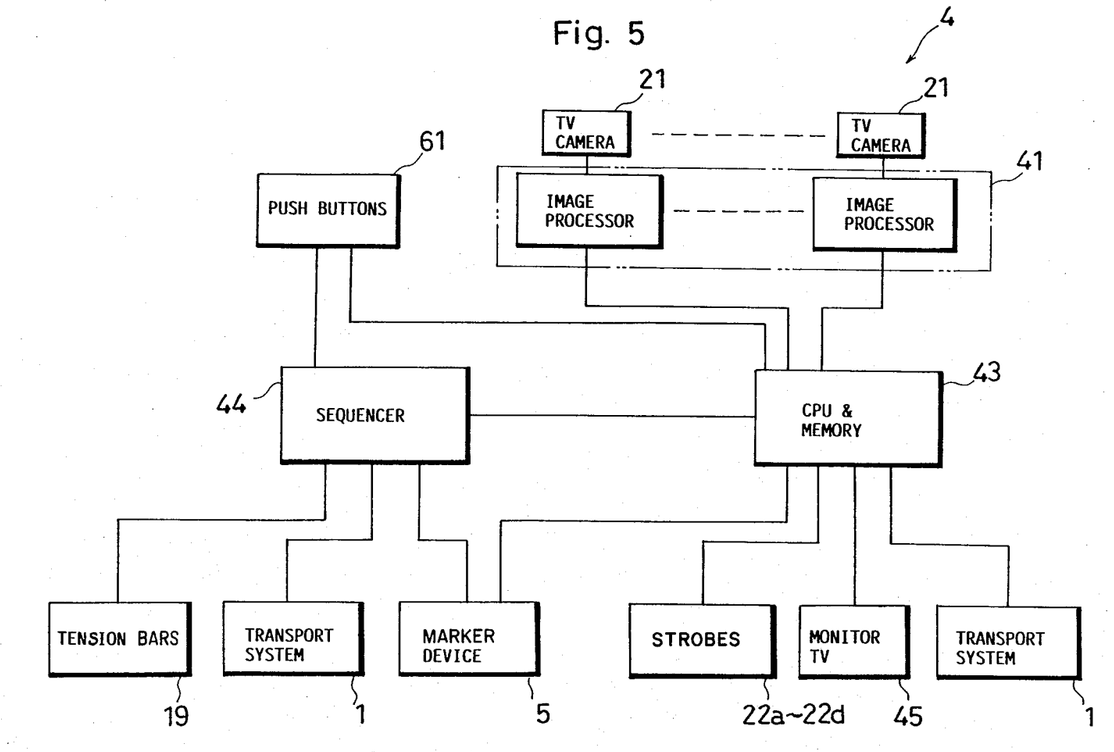
FIG. 5 is a block diagram of a processing device forming part of the fabric inspecting apparatus.

Referring to FIG. 5, the processing device 4 comprises an image processing unit 41 for processing the images obtained through the TV cameras 21, a data processing unit 43 including a CPU 42 and a memory for receiving signals from the image processing unit 41, calculating flaw positions and controlling the transport system 1 and marker devices 5, and a sequencer 44 for providing sequence controls. These operations will particularly be described with reference to the flowcharts later. Number 45 indicates a monitor TV for confirming the image provided by a selected TV camera 21.

Figure 6:
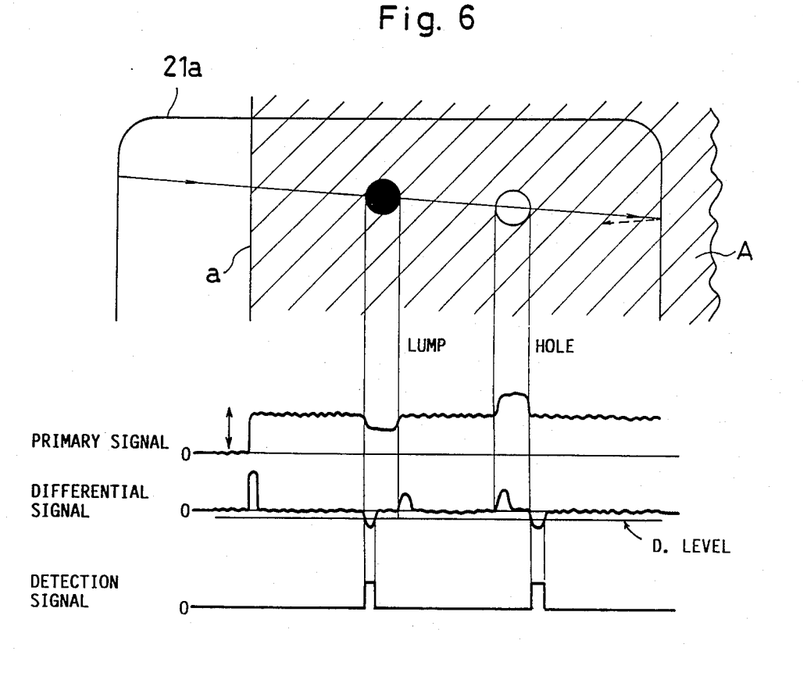
FIG. 6 is a view illustrating an operation for obtaining detection data during one scan of one of the TV cameras shown in FIG. 2.
Figure 7:
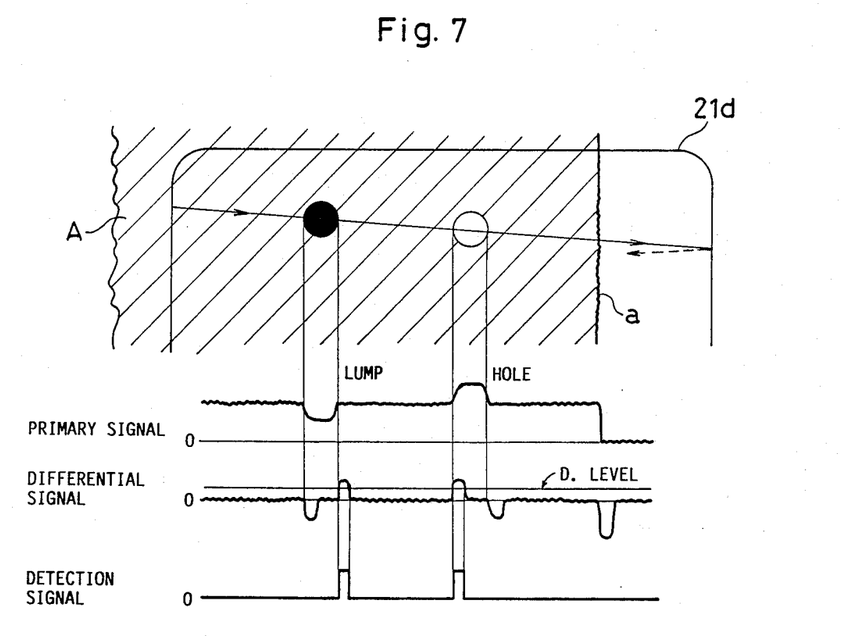
FIG. 7 is a view illustrating an operation for obtaining detection data during one scan of another TV camera shown in FIG. 2, FIG. 8 (a) is a front view of a marker device, FIG. 8 (b) is a side view of the marker device.

The image processing unit 41 comprises a circuit for obtaining differential signals from primary signals provided by TV cameras 21a-21f and delay signals delayed a fixed time after the primary signals as shown in FIGS. 6 and 7 (such a circuit may comprise a delay element, a differential amplifier and a comparator), and a strobe synchronizing circuit for synchronizing the image pickup action of TV cameras 21a-21f and light emission of strobes 22a-22d.

FIG. 6 is a view for illustrating an operation for obtaining detection data during one scan of TV camera 21a in FIG. 2. A detection level is set low with respect to a reference signal in order to avoid a differential signal from a selvage a of fabric A being taken as a valid signal. FIG. 7 is a view for illustrating an operation for obtaining detection data during one scan of TV camera 21d. Since the selvage a of fabric A is at an opposite position in this case, the detection level is set high in order to detect only flaw positions accurately.

Figure 8A:
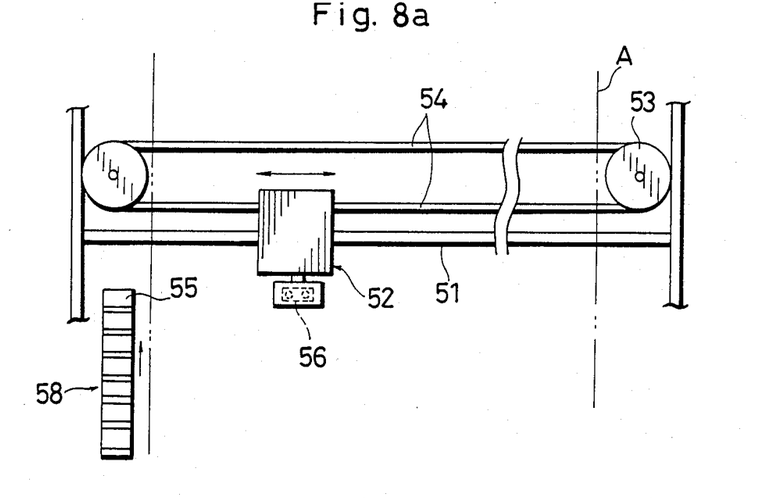
Figure 8B:
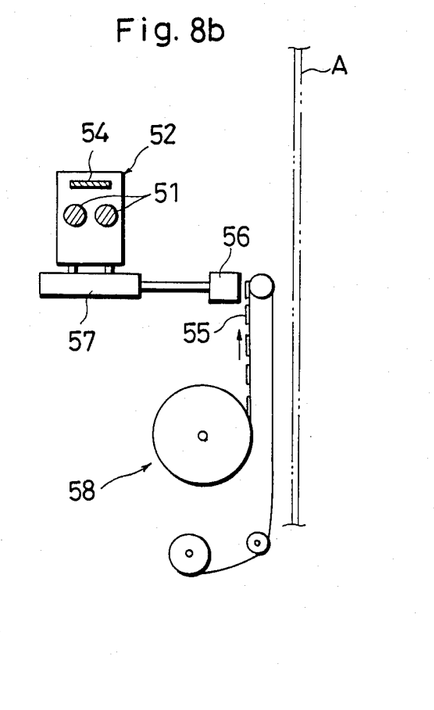

As shown in FIGS. 8 (a) and (b), each marker device 5 comprises support rods 51 extending transversely of the fabric A, and a main marker member 52 mounted on the support rods 51 for reciprocal movements. The main marker member 52 is movable to selected positions by a timing belt 54 driven by a pulley 53 connected to a stepper motor. A head 56 is attached to the main marker member 52 through an air cylinder 57 for adsorbing marks 55 and pressing and applying the marks 55 to the fabric A. A mark feeder 58 for supplying the marks 55 is fixed at an end of the support rods 51. Two marker devices 5 are symmetrically arranged across the fabric A to carry out the same operation.

A fabric inspecting method will be described now in relation to the operation of the foregoing fabric inspecting apparatus. The fabric A to be inspected is drawn upward by the takeup roller 12 from the table 11a of the supply section and is placed on the belt conveyor 13a. The fabric A is transported by the belt conveyor 13a and then by the belt conveyor 13b which is disposed substantially horizontal at a low position. A fabric hold 18 having a U-shaped section is connected to the rear end of the belt conveyor 13b for temporarily arresting the fabric A in transport. The fabric A is drawn upward from the fabric hold 18 to the upper belt conveyor 13c by way of the dark room 2, advancing through the slit 3 of the dark room 2. A tension bar device 19 is provided at a bottom of the dark room 2, which comprises a stationary bar 19a and a spring-loaded movable bar 19b for causing the fabric A to run about halfway around the stationary bar 19a. The tension bar device 19 serves to avoid development of creases or the like on the fabric A drawn up by the belt conveyor 13c. The fabric A transported from the belt conveyor 13c to the table 11b of the receiving section is folded by the swing folding device 14 into the form as in the supply section.

Figure 4:
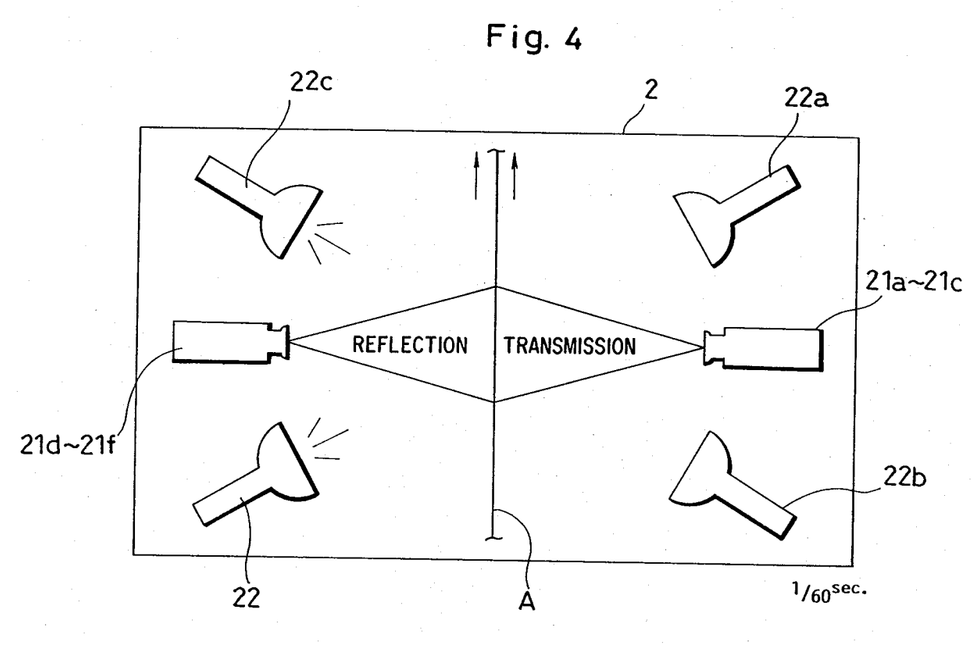
FIG. 4 is a side view of the dark room showing a state in which strobes at an opposite side emit light to the fabric.

In the dark room 2 disposed on the fabric transport path, the strobes 22a and 22b at one side of fabric A and the strobes 22c and 22d at the other side take turns every 60th second at emitting light to illuminate the fabric A.

FIGS. 3 and 4 illustrate this state. The strobes 22a–22d are located outside the fields of view of all TV cameras 21. Consequently, when the strobes 22a and 22b at one side emit light as shown in FIG. 3, the TV cameras 21a–21c at the same side pick up reflection images of the fabric A whereas the TV cameras 21d–21f at the other side pick up transmission images of the fabric A. When the strobes 22c and 22d at the other side emit light as shown in FIG. 4, the TV cameras 21 pick up reflection and transmission images opposite to the above.

Figure 2B:
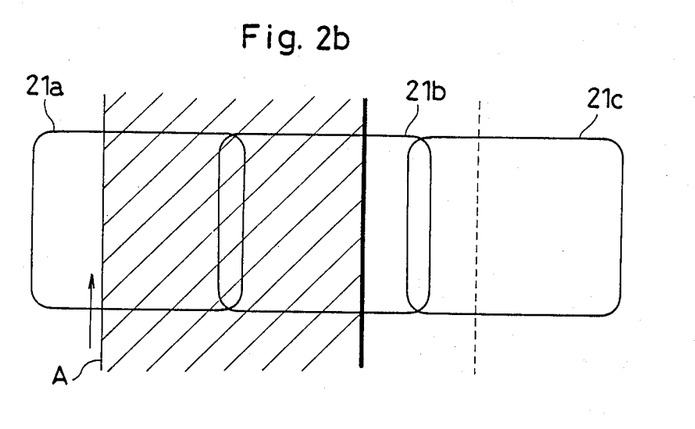
FIG. 2(b) is a view showing a relationship between a fabric and image ranges picked up by TV cameras at one side of the fabric.

As shown in FIG. 2, the three TV cameras 21a–21c or 21d–21f are arranged at intervals transversely of the fabric A. This arrangement permits a single inspecting apparatus to cope with fabrics A having various widths, and expedites the inspection by dividing the fabric image for inspection. In the illustrated example, the fabric A has a width fitting in the fields of view of two TV cameras 21a and 21b or 21c and 21d at either side.

When a flaw is detected, the marker devices 5 are operated in response to processing results and control signals output from the processing device 4 to actuate the respective heads 56 to adsorb marks 55 from the mark feeders 58. The heads 56 are then driven through the timing belt 54 by the pulleys 53 connected to the stepper motor to move to the selvage of fabric A. Thereupon the air cylinders 57 push the heads 56 to apply the marks 55 to the fabric A so that halves of the marks 55 project from the selvage and bond to each other.

After the marks 55 are applied to the selvage, the heads 56 return to the positions to adsorb marks 55. This time only one of the heads 56 adsorbs mark 55 for application to the face of fabric A on which the flaw is found. Then both heads 56 are moved and pressed against each other so as to sandwich the fabric A at a flaw position calculated by the processing device 4. At this time the head 56 not carrying the mark 55 acts as a backup for supporting the fabric A from the back.

Figure 9:
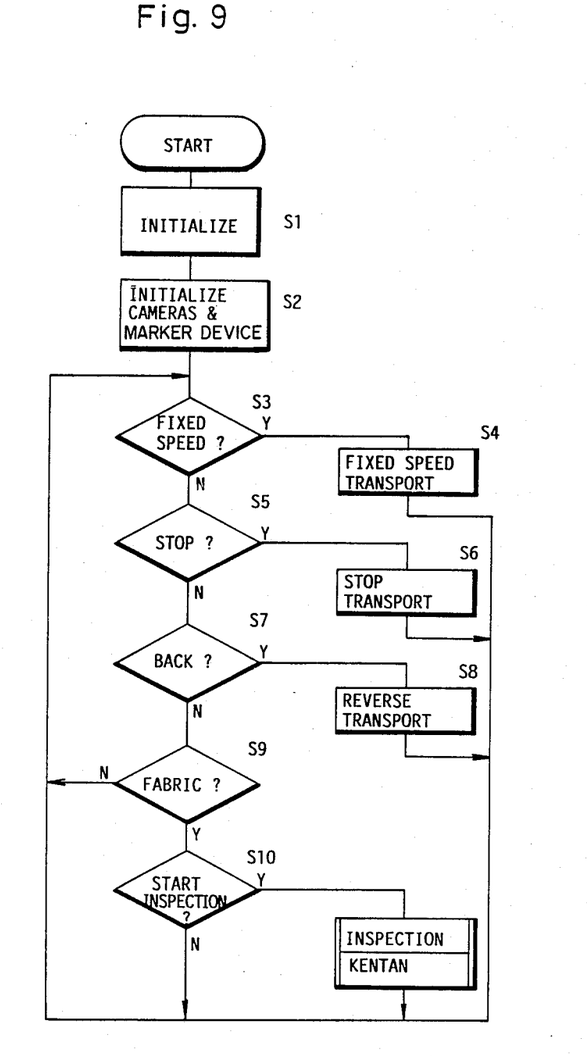
FIGS. 9 through 12 are flowcharts illustrating operations of the processing device.

Operations will be described next with reference to the flowcharts shown in FIGS. 9 through 12. The flowchart of FIG. 9 illustrates a routine preparatory to the operation of the described apparatus. First, judgment is made whether an automatic inspection should be started by confirming ON-OFF states of push buttons 61 for a manual operation shown in FIG. 1, and whether the fabric A is transported or not is judged. In other words, the processing device 4 is initialized at step S1, and TV cameras 2 and marker device 5 are initialized at step S2. Then, whether a fixed speed transport button among the push buttons 61 is pressed or not is checked at step S3. If the fixed speed transport button is pressed, step S4 starts transport of fabric A at a fixed speed and makes a return to step S3. If not, step S5 checks whether a transport stop button is pressed or not. If this button is pressed, step S6 stops transport of fabric A and makes a return to step S3. If not, step S7 checks whether a transport reversing button is pressed or not. If it is, step S8 causes a backward transport of fabric A and makes a return to step S3. If none of the above three buttons are pressed, step S9 judges whether the fabric A is running through the dark room 2 or not. If it is, step S10 judges whether the automatic inspection should be carried out. Then a subroutine is executed for the automatic inspection.

Figure 10:
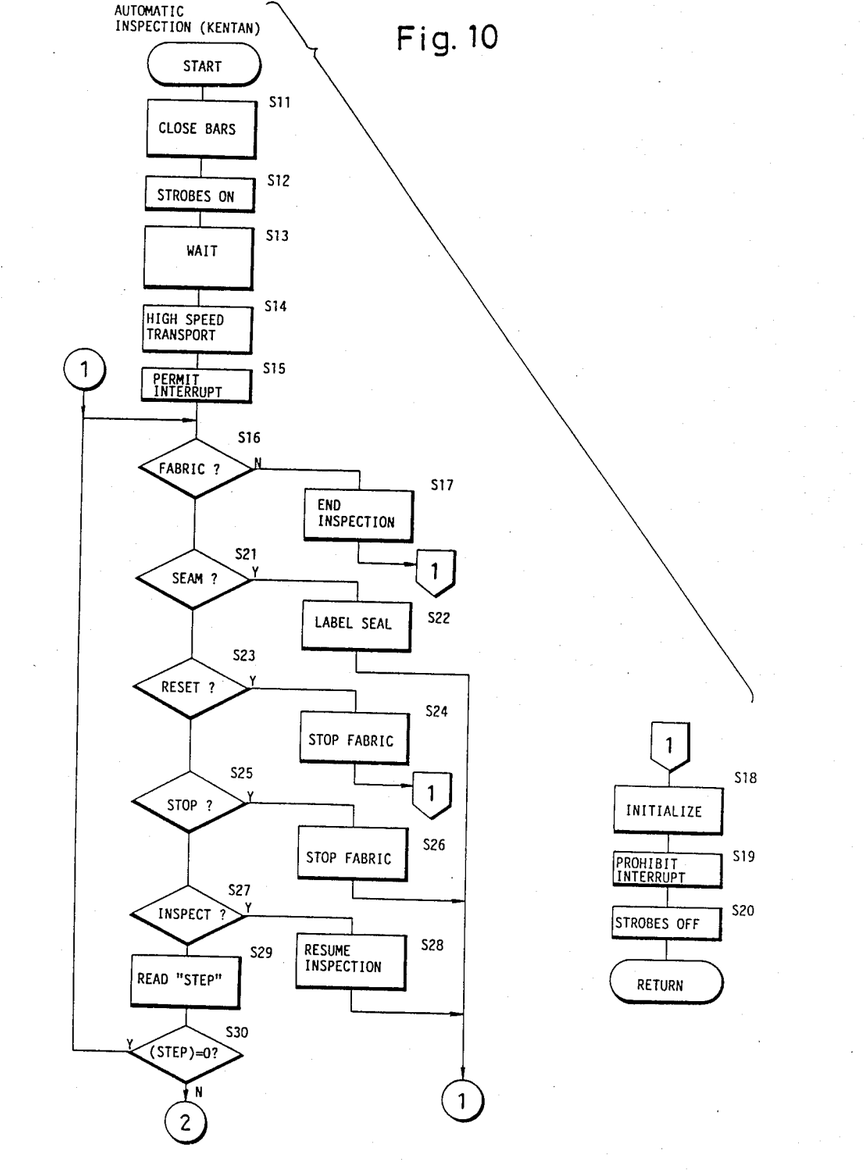

The automatic inspection is carried out according to the flowchart shown in FIG. 10. First, the tension bar device 19 is closed at step S11 to stabilize the fabric A in transportation. At step S12, strobes 22 are turned on by pulses output from the strobe synchronizing circuit of the image processing unit 41 in synchronism with video signals of TV cameras 21. The strobes 22 are controlled such that the strobes 22a and 22b at one side and strobes 22c and 22d at the other side take turns every 60th second at emitting light. Next, step S13 turns on TV cameras 21 and wait in this state until automatic aperture setting is stabilized. Then step S14 starts transporting the fabric A at high speed by controlling the drive motor 15 of transport system 1 comprising a servomotor. Thereafter, step S15 permits an interrupt by an interrupt routine regardless of all operations at the subsequent steps.

At step S16, the photoswitch determines presence or absence of the fabric A. If there is no fabric A, inspection is no longer required and all transport control is terminated at step S17. Then the processing device 4 is initialized at step S18, and the interrupt is prohibited at step S19, and the strobes 22 are turned off to bring the inspection to an end.

If, on the other hand, fabric A is transported, the photoswitch searches for a seam at step S21. If a seam is found, a corresponding signal is supplied to the marker device 5 at step S22 to apply the marks 55 at the selvage of fabric A as already described. In the absence of a seam, the program moves from step S21 to step S23 and judges whether a reset button among the push buttons 61 is pressed or not. If it is pressed, step S24 stops the fabric A and moves to step S18 for stopping the inspection routine.

If the reset button is off at step S23, step S25 judges whether the transport stop button is pressed or not. If it is, the fabric transport is stopped at step S26 and the program returns to step S16.

If the transport stop button is off at step S25, step S27 judges whether an inspection start button is pressed or not. When this button is pressed, the program returns from step S28 to step S16 for starting the inspection. This inspection start button is provided for resuming the inspection after the inspection is suspended by means of the transport stop button or others.

Figure 11:
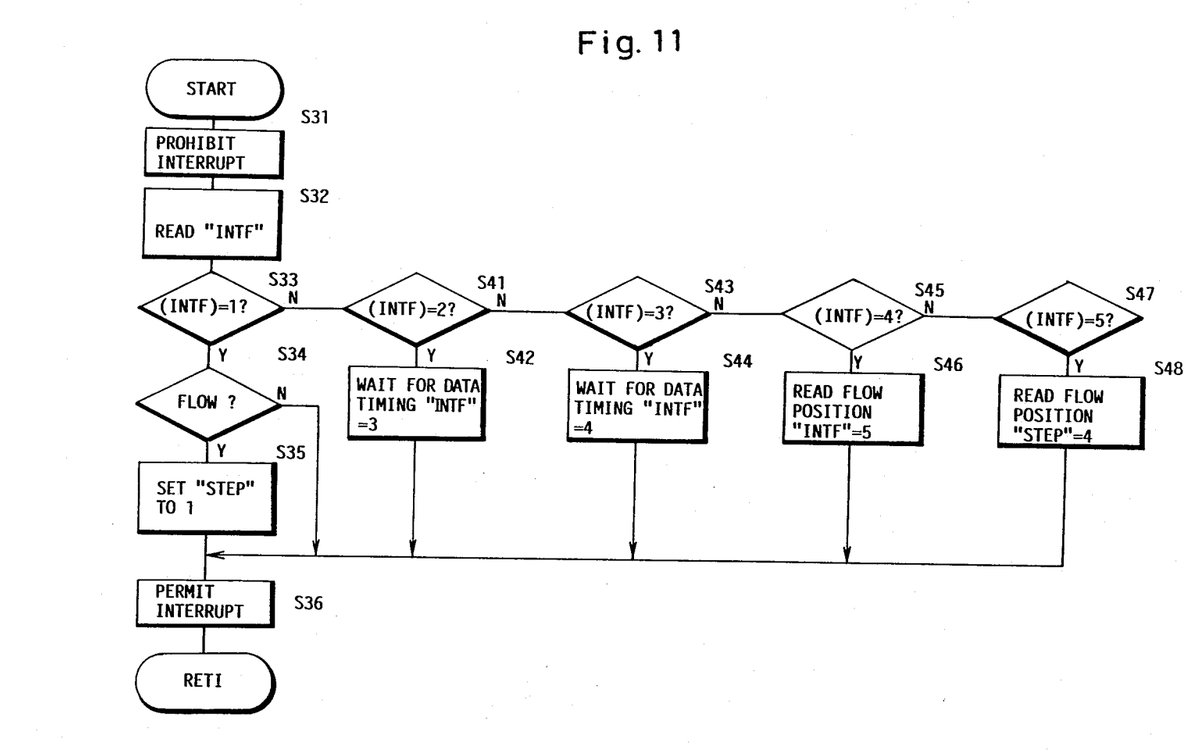

Next, when the inspection start button changes to OFF at step S27, step S29 reads status flag "STEP" in the memory. This status flag indicates a current state of the inspecting apparatus, and the status flag identified by the number of "STEP" is changed every time the components of the inspecting apparatus completes one operation. For example, status flag "0" indicates that no flaw is detected by the inspecting apparatus, status flag "1" indicates detection of a flaw, status flag "2" indicates the fabric transport being stopped, and so on. In this way, 12 states in total from "0" to "11" are provided. When the status flag is "0", the program returns to step S16 and repeats the routine from step S16 to step S30 while no flaw is detected in the fabric A. Upon detection of a flaw in the course of repeating these steps, an interrupt takes place and the interrupt routine shown in FIG. 11 is executed. This interrupt routine prohibits a further, unillustrated interrupt at step S31, reads an interrupt flag INTF in the memory at step S32, and judges at step S33 whether the interrupt flag INTF is "1" or not. This interrupt flag INTF has an initial value set to "1", and is set to "2" when a flaw is detected at step S34 described later. While the interrupt flag INTF remains "1", that is while no flaw is detected, the operation is carried out bypassing step S35.

When a flaw detection signal is input to CPU 42, the program moves from step S34 to step S35 at which the status flag "STEP" is set to "1". After permitting the unillustrated, other interrupt at step S35, the program returns to the inspection routine. In the inspection routine, the program moves from step S30 to the flowchart following encircled numeral 2 shown in FIG. 12 since the status flag "STEP" is "1". Through steps S51 and S52, the fabric transport is made to slow down to a stop and the status flag "STEP" is incremented to "2". Then the program returns to step S16 and repeats the operation up to step S51. Since the status flag "STEP" is "2" at step S51, the program moves to steps S53 and S54 to transport the fabric A a fixed distance backward and increment the status flag "STEP" to "3". This fixed distance is slightly longer than a distance the fabric advances after detection of a flaw. Thereafter, the program returns to step S16 again and repeats the operation up to step S55. Since the status flag "STEP" is "3" this time, the program moves on to step S56. At step S56, flaw data are read from the TV cameras and, therefore, the interrupt flag INTF read at step S32 of the interrupt routine is set to "2".

When the interrupt flag INTF is set to "2", the interrupt routine is executed again. The interrupt routine moves from step S33 rightward to steps S41 and S42 to wait for data timing and increment the interrupt flag INTF to "3". Then, step S36 permits an interrupt and executes the interrupt routine again. In the second execution, the interrupt routine moves to steps S43 and S44 to increment the interrupt flag INTF to "4". Thereafter, every time the interrupt flag INTF is incremented and the interrupt is permitted at step S36, the interrupt routine is executed to read coordinates of the flaw at steps S46 and S48. At the last step S48, the status flag "STEP" is set to "4". If the coordinates of the flaw are obtained by the light reflected by the fabric at step S46, then then the coordinates obtained at step S48 is by the light transmission through the fabric.

Figure 12:
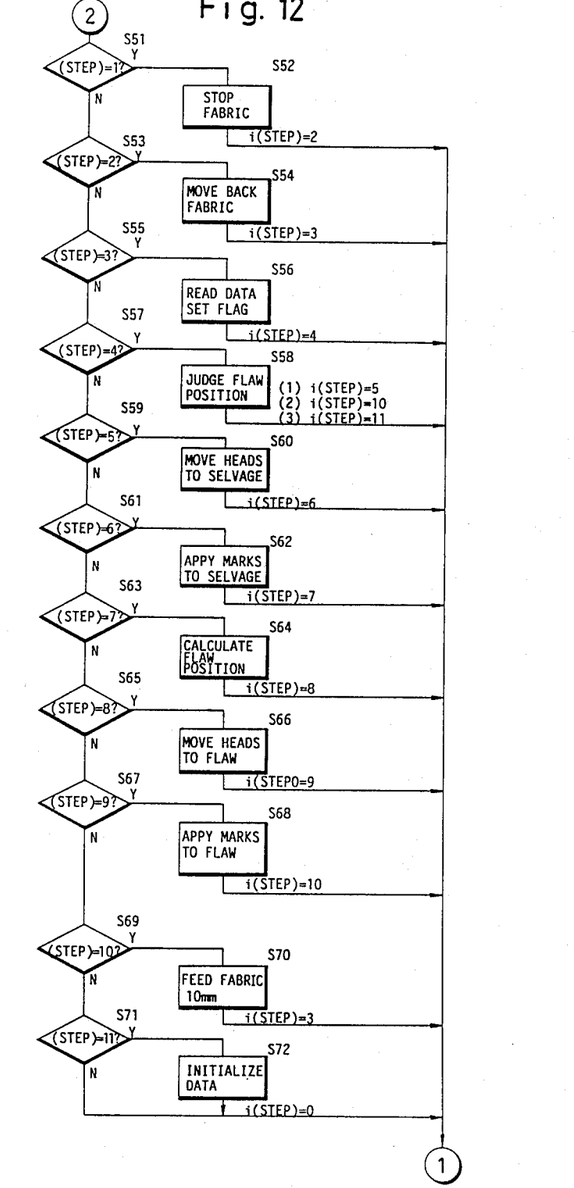

After completing step S48, the program returns through step S36 to the inspection routine which is the main routine. Since the status flag "STEP" is set to "4" in this case, the inspection routine moves from step S57 to step S58 to determine the flaw position in the fabric. That is, step S58 judges X-Y coordinates which are the read flaw signal data, and one of the following three operations:

(1) increment "STEP" to "5" when the flaw is found at the position to which the marks are applied, (2) increment "STEP" to "10" when the flaw is found between the position to which the marks are applied and the image position picked up by the TV cameras 21, and (3) increment "STEP" to "11" when the flaw is not found between the position to which the marks are applied and the image position picked up by the TV cameras 21.

When the status flag "STEP" is incremented to "5", the program proceeds to steps S59 and S60 to move the heads 56 of the marker devices 5 to the selvage of fabric A and increment the status flag "STEP" to "6". After executing each of steps S62, S64, S66, S68 and S70 the program returns to step S16 and executes an operation up to the step indicated by the status flag "STEP" for applying the marks 55 to the selvage and the position of the flaw on the fabric A. Step S68 completes the series of operations relating to one flaw. Then, at step S70, the fabric is advanced just 10 mm and a similar process is repeated.

When the flaw is found between the marker device 5 and TV cameras 21 as in the case (2) above, the program jumps to step S70 without executing the intervening steps as above. The fabric advance of step S70 is repeated till a next flaw is detected.

When there is no flaw as in the case (3) above, the program jumps to step S72 to initialize the flaw data (i.e. the X-Y coordinates), set the status flag "STEP" to "0", and return to step S16. The routine is thereafter executed from step S16 to step S29 until a flaw is detected. In this case the fabric A is transported at high speed as controlled at step S14. When a flaw is detected, the fabric A is stopped and transported backward for redetection and marking, and then is advanced 10 mm as described above. When the fabric has been inspected throughout, the program moves from step S16 to step S17 to terminate the inspection.

According to the fabric inspecting method and apparatus as described, the strobes 22 are actuated to illuminate the faces of fabric A obliquely from above, taking turns every 60th second (or 1/60 second). The TV cameras arranged at opposite sides across the fabric A receive the light reflected from the fabric and the light having passed through the fabric, and the images thus obtained are put to analysis. Consequently, lump type and void type flaws developing in complex forms in the fabric are now detected in a reliable manner. The described method and apparatus provide a greatly improved detecting precision.

Although the present invention has been fully described by way of example with reference to the accompanying drawings, it is to be noted that various changes and modifications will be apparent to those skilled in the art. Therefore, unless otherwise such changes and modifications depart from the scope of the present invention, they should be construed as being included therein.

What is claimed is:

1. A method of inspecting a fabric in strip form to find flaws comprising the steps of;
    transporting the fabric through a space between a plurality of strobes and image pickup elements, and alternately causing the strobes at one side of the fabric and the strobes at the other side to emit light,
    causing the image pickup elements at both sides of the fabric to read strobe light passing through the fabric and strobe light reflected by the fabric at times of light emission from the strobes,
    detecting a flaw on the fabric by electrically processing images provided by the image pickup elements, and
    marking the fabric at a position of the flaw.

2. A method as claimed in claim 1, wherein said step of detecting a flaw includes the step of detecting the flaw again by stopping the fabric, transporting the fabric a predetermined distance backward and then advancing the fabric at low speed.

3. An apparatus for inspecting a fabric in strip form to find flaws comprising,
    transport means for transporting the fabric longitudinally thereof,
    a dark room through which the fabric is transported,
    a plurality of strobe means arranged in the dark room to emit light to the fabric in transportation alternately from opposite sides thereof,
    image pickup means associated with the strobe means to pick up strobe light passing through the fabric and reflected by the fabric, processing means for electrically processing images provided by the image pickup means, and marking means for marking a flaw position of the fabric in response to a flaw signal received from the processing means.

4. An apparatus as claimed in claim 3, wherein said strobe means are arranged at both sides of the fabric and outside fields of view of said image pickup means.

5. An apparatus as claimed in claim 3, wherein said image pickup means are provided in a plural number and arranged at intervals transversely of the fabric.

6. An apparatus as claimed in claim 3, wherein said marking means is controlled to apply marks to the flaw position and to a selvage of the fabric.

* * * * *